United States Patent
Podszun et al.

Patent Number: 5,328,804
Date of Patent: Jul. 12, 1994

[54] IMAGE PRODUCING ELEMENT CONTAINING A PHOTOPOLYMERIZABLE MONOMER

[75] Inventors: Wolfgang Podszun, Cologne; Michael Müller, Bergisch Gladbach, both of Fed. Rep. of Germany; Herman Uytterhoeven, Bonheiden, Belgium

[73] Assignee: Agfa Gevaert Aktiengesellschaft, Leverkusen, Fed. Rep. of Germany

[21] Appl. No.: 932,963

[22] Filed: Aug. 20, 1992

[30] Foreign Application Priority Data

Sep. 3, 1991 [DE] Fed. Rep. of Germany ....... 4129284

[51] Int. Cl.$^5$ ............ G03F 7/031; G03C 1/805
[52] U.S. Cl. .................... 430/283; 430/270; 430/254; 430/358; 430/260; 430/288
[58] Field of Search ............ 430/283, 358, 260, 288, 430/270, 254

[56] References Cited

U.S. PATENT DOCUMENTS

| | | | |
|---|---|---|---|
| 3,060,023 | 10/1962 | Burg | 430/254 |
| 3,060,024 | 10/1962 | Burg | 430/254 |
| 3,085,488 | 4/1963 | Helart | 355/100 |
| 3,245,796 | 4/1966 | Burg | 430/201 |
| 3,622,320 | 11/1991 | Allen | 430/254 |
| 3,649,268 | 3/1972 | Chu | 430/291 |
| 3,856,830 | 12/1974 | Kuehn | 528/80 |
| 4,019,972 | 4/1977 | Faust | 430/283 |
| 4,145,544 | 3/1979 | Kuehn | 544/222 |
| 4,315,066 | 2/1982 | Lambert | 430/271 |
| 4,587,198 | 5/1986 | Fisch | 430/201 |
| 4,920,037 | 4/1990 | Takahashi et al. | 430/287 |

FOREIGN PATENT DOCUMENTS

| | | |
|---|---|---|
| 0107336 | 10/1980 | European Pat. Off. . |
| 0125862 | 11/1984 | European Pat. Off. . |
| 0249468 | 12/1987 | European Pat. Off. . |
| 0362827 | 11/1990 | European Pat. Off. . |

Primary Examiner—Charles L. Bowers, Jr.
Assistant Examiner—Mark F. Huff
Attorney, Agent, or Firm—Connolly and Hutz

[57] ABSTRACT

Transfer images with high resolution are obtained with an image producing element containing a layer of a photopolymerisable composition with a monomer of Formula I by imagewise exposure and transfer of the unhardened parts of the photopolymerisable composition to an acceptor material.

$$A[-R^1-NHCO-X-R^2(-OCO-\underset{|}{\overset{R^3}{C}}=CH_2)_n]_m \quad (I)$$

In Formula I
  A denotes a double-bonded or triple-bonded condensed urea group;
  X denotes O or NR in which R=$C_1$-$C_{12}$-alkyl;
  $R^1$ denotes a double-bonded hydrocarbon group having 2 to 25 carbon atoms;
  $R^2$ denotes a double-bonded to six-bonded linear or branched hydrocarbon group with 2 to 18 carbon atoms optionally interrupted by up to 3 O atoms;
  $R^3$ denotes H or methyl;
  n denotes an integer from 1 to 5 and
  m stands for 2 or 3.

18 Claims, No Drawings

IMAGE PRODUCING ELEMENT CONTAINING A PHOTOPOLYMERIZABLE MONOMER

The present invention relates to an image producing element containing a photopolymerisable monomer of Formula I.

The use of photopolymerisation for the production of copies by imagewise exposure with actinic rays is known. The method of copying is based on the principle of producing a differentiation of the properties of the exposed and unexposed parts of a photopolymerisable layer, for example a differentiation with respect to solubility, adhesion, conductivity, refractive index, tackiness, permeability or diffusibility of penetrating substances such as dyes.

Copying systems based on a differentiation of the tackiness are described in U.S. Pat. Nos. 3,060,024, 3,085,488 and 3,649,268. In the method disclosed in these U.S. Patent Specifications, the photopolymerisable layer loses its tackiness in the imagewise exposed areas while the unexposed areas remain tacky. The unexposed areas can therefore be coloured with dry pigments to render the image visible.

Other copying methods based on photopolymerisation followed by dry development are described in U.S. Pat. No. 3 245 796, EP-A-0 362 827, U.S. Pat. No. 4 587 198 and U.S. Pat. No. 3 060 023.

Photopolymerisation is used in various ways for the reproduction of images. Both methods with wet image development and methods with dry image development are employed. The latter are particularly user friendly and have decided ecological advantages.

The resolution which can be obtained with dry developable photopolymerisable compositions is, however, relatively poor, and this is a special problem in the reproduction of finely rastered images.

It is an object of the present invention to provide an image producing element which contains a photopolymerisable composition, is developable by the application of heat and can provide a high resolution.

The invention relates to an image producing element containing a layer of a photopolymerisable composition characterised by a photopolymerisable content of at least one monomer corresponding to the following Formula I $$A[-R^1-NHCO-X-R^2(-OCO-\underset{|}{\overset{R^3}{C}}=CH_2)_n]_m,\quad (I)$$

wherein
  A denotes a double-bonded or triple-bonded condensed urea group;
  X denotes O or NR in which R=$C_1$-$C_{12}$-alkyl;
  $R^1$ denotes a double-bonded hydrocarbon group having 2 to 25 carbon atoms;
  $R^2$ denotes a double-bonded to six-bonded linear or branched hydrocarbon group with 2 to 18 carbon atoms optionally interrupted by up to 3 O-atoms;
  $R^3$ denotes H or methyl;
  n denotes an integer from 1 to 5 and
  m stands for 2 or 3.

The following structural units are examples of condensed urea groups denoted by A:

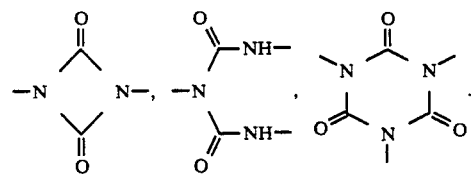

The double-bonded group denoted by X is preferably oxygen (—O—). When X stands for —NR—, R is a linear or branched alkyl group; examples are methyl, ethyl, propyl and t-butyl.

The hydrocarbon group with 2 to 25 carbon atoms denoted by $R^1$ may be interrupted by oxygen. It is an aliphatic, aromatic or mixed aliphatic-aromatic hydrocarbon group. $R^1$ may, for example, stand for a double-bonded straight-chained or branched aliphatic group, preferably with 2 to 12 carbon atoms. The following are examples: Ethylene, propylene, 1,4-tetramethylene, 1,6-hexamethylene and 2,2,4-trimethyl-1,6-hexamethylene and possibly isomers thereof.

$R^1$ may also stand for a mono- or polycyclic saturated or aromatic hydrocarbon group having 6 to 24 carbon atoms, preferably 6 to 14 carbon atoms, for example the following:

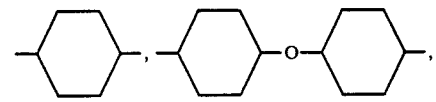

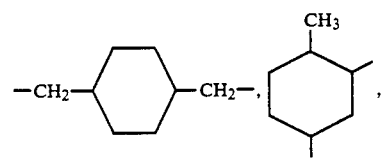

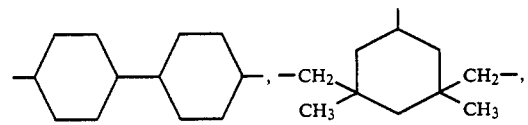

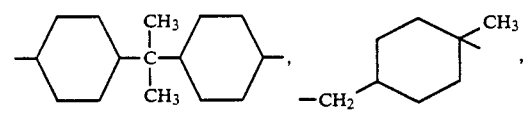

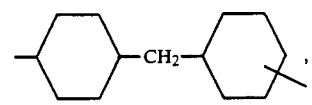

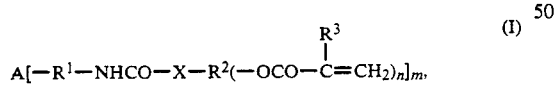

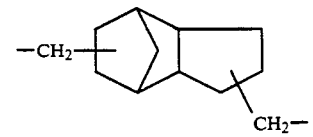

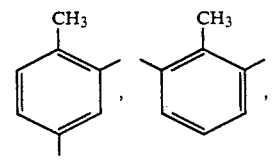

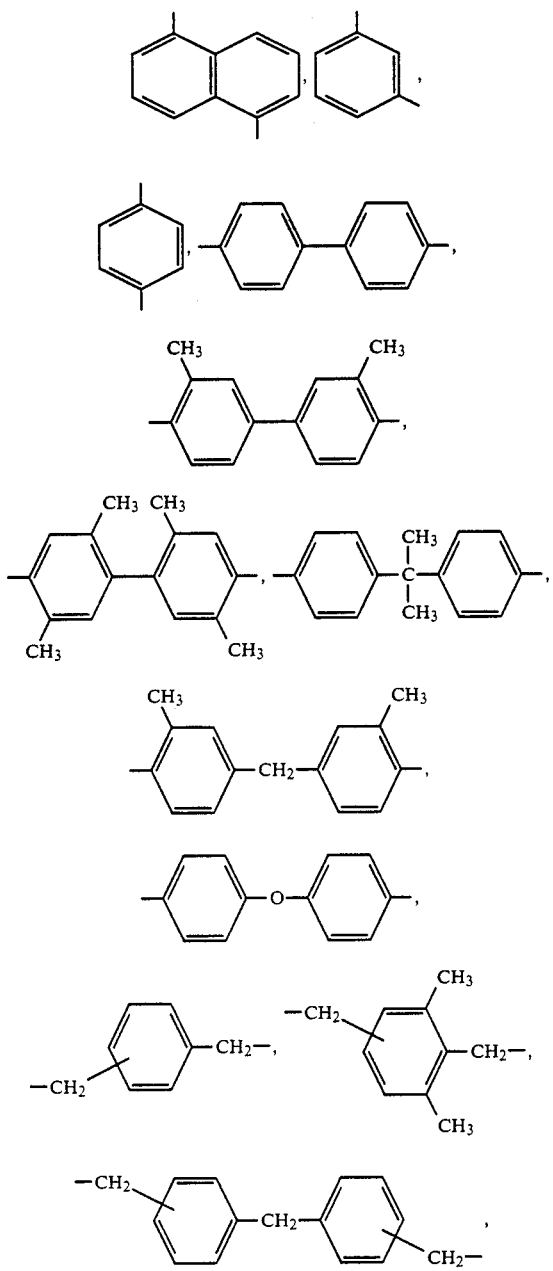

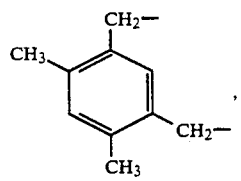

The hydrocarbon group denoted by $R^2$ optionally interrupted by O atoms is preferably a double bonded to four-bonded group having 2 to 12 carbon atoms. The following are examples:

Ethylene, propylene and 1,2-butylene; the following multibonded groups, for example, are also suitable:

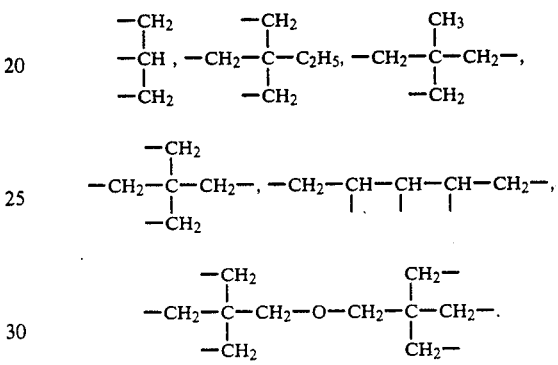

n preferably stands for 2 or 3.

Particularly preferred is an image producing element containing a monomer corresponding to Formula I wherein X stands for —O—;

$R^1$ stands for an aliphatic or cycloaliphatic group having 5 to 8 carbon atoms;

$R^2$ stands for a triple-bonded or four-bonded hydrocarbon group (n=2 or 3) having 3 to 6 carbon atoms;

R3 stands for H or methyl.

Some compounds are new; examples of new monomers are M-3, M-4, M-5 and M-6 shown below.

The compounds shown in Table 1 below are examples of polyfunctional monomers which are particularly suitable for the present invention.

TABLE 1

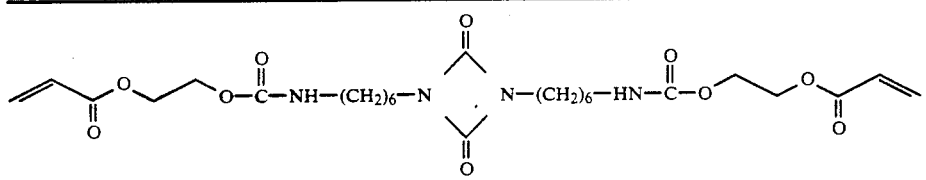

M-1

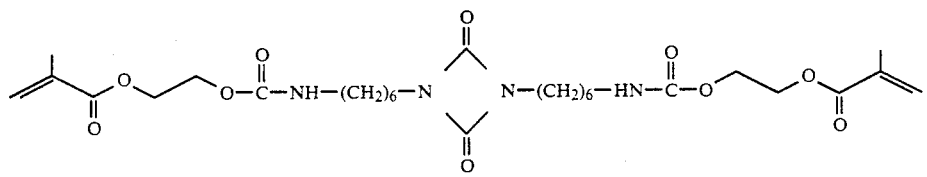

M-2

TABLE 1-continued
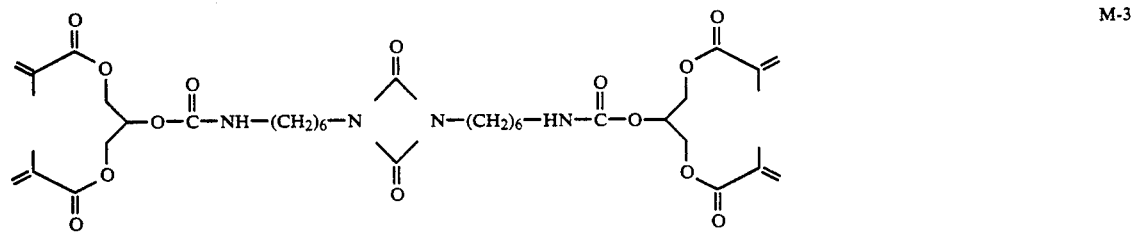
M-3
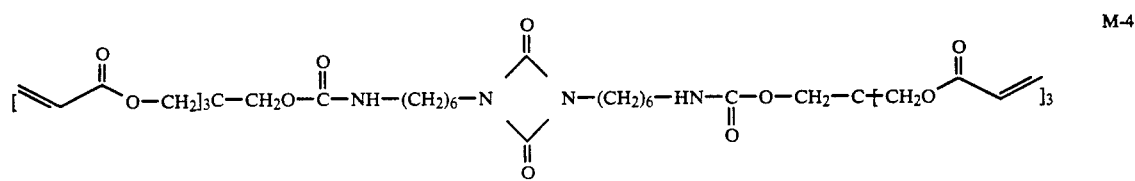
M-4
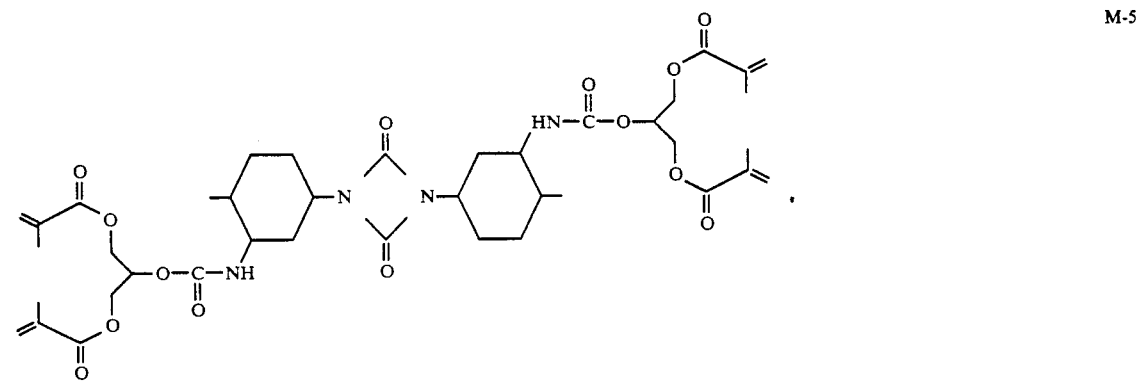
M-5
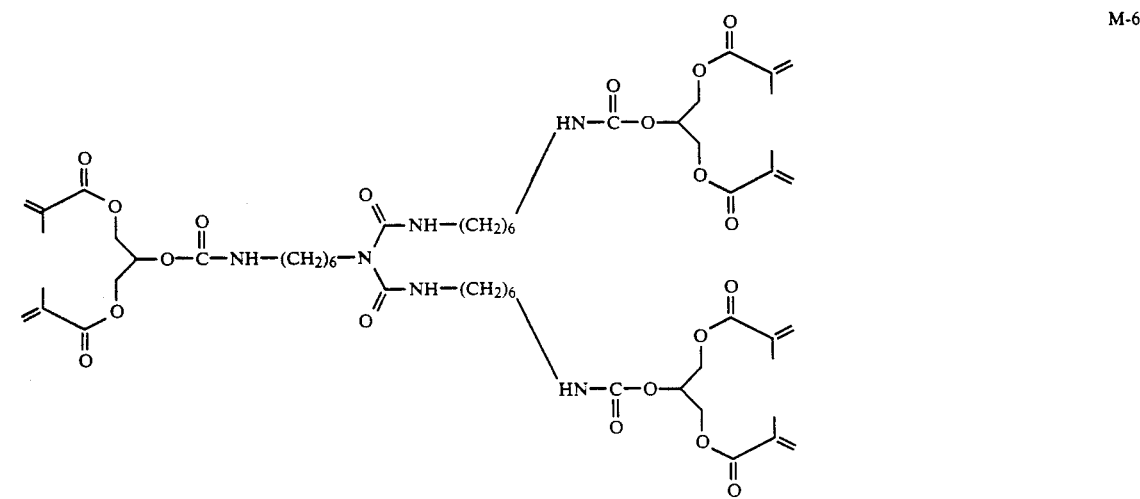
M-6

TABLE 1-continued

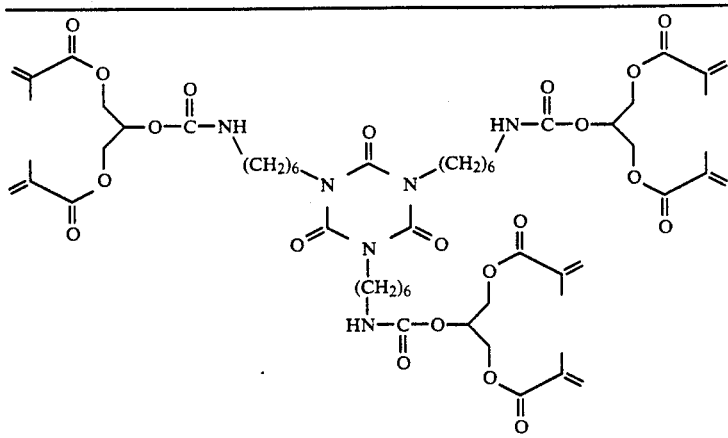

M-7

It was found that the multifunctional monomers according to the invention are very readily photopolymerisable and undergo solidification and hence a marked decrease in tackiness and thermal transferability even at low conversion rates, e.g. of the order of 10%, so that rapid differentiation can be achieved between exposed and unexposed areas.

The multifunctional (meth)acrylates are synthesized by the reaction of diisocyanates or triisocyanates with hydroxy-alkyl(meth)acrylates or N-alkylated aminoalkyl(meth)acrylates in accordance with the following reaction scheme:

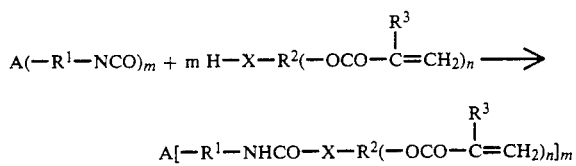

This synthesis may be carried out solvent-free if the reactants are of low viscosity, but the use of an inert solvent is advantageous in many cases. A catalyst is generally used. When $R^1$ is an aromatic group, the catalyst may be omitted. The reaction temperature is in the range of from 0° to 120° C., preferably from 20° to 60° C. The progress of the reaction may be monitored by checking the isocyanate content by IR spectroscopy and/or titration.

Examples of suitable solvents include acetone, methyl ethyl ketone, chloroform, tetrahydrofuran, dioxane, methylene chloride, toluene and acetonitrile.

The synthesis is generally carried out with substantially complete exclusion of water. It is particularly preferred to use less than 0.1% by weight of water, based on the total quantity of reactants.

Catalysts for the synthesis are generally metal salts of higher fatty acids. Preferred catalysts are, for example, dibutyl tin laurate, dibutyl tin methoxide and tin-(II)-octoate. The catalysts may also be compounds containing tertiary amino groups, such as triethylamine, pyridine, 2-methylpyridine, N,N-dimethylpiperazine and N,N-dimethylbenzylamine. Titanium compounds such as tetrabutyltitanate may also be used.

The catalyst is generally used in a quantity of from 0.1 to 2.5% by weight, preferably from 0.1 to 1.5% by weight, based on the total quantity of reactants.

In a preferred embodiment, synthesis may be carried out in the presence of a polymerisable inhibitor.

Polymerisation inhibitors are known per se (Ullmanns Enzyklopädie der techn. Chemie, 4th Edition, Publishers Verlag Chemie Weinheim, Volume 8, pages 19-45). 2,6-Di-tert.-butyl-4-methylphenol, hydroquinone and hydroquinone monomethylether are mentioned as examples.

Oxygen may also be used as polymerisation inhibitor, e.g. atmospheric oxygen which is passed through the reaction mixture.

The polymerisation inhibitor is generally used in a quantity of from 0.01 to 1.0% by weight, preferably from 0.1 to 0.2% by weight.

The photopolymerisable composition is exposed to actinic radiation in imagewise distribution so that it will be hardened according to the imagewise distribution of the actinic radiation. This exposure may be in the form of contact exposure with ultraviolet rays, exposure by camera, linewise exposure (scanning exposure) or exposure to laser. The source of light may be daylight, incandescent lamps, mercury vapour lamps, halogen lamps, Xenon lamps, fluorescent lamps, light emitting diodes, lasers, electron beams or X-rays.

In a preferred embodiment of the present invention, the monomers corresponding to the general Formula I are contained in a thermoplastic layer of a thermoplastic polymer applied to a layer support, preferably in a quantity of from 3 to 97% by weight. After imagewise exposure, the image producing element according to the invention (donor element) or an acceptor element or both are heated separately before they are brought into contact with one another or heating takes place while the donor element and the acceptor element are in contact. After heating and imagewise transfer, the donor element and acceptor element may be separated.

The thermoplastic layer mentioned above is preferably solid at temperatures below 40° C. At temperatures from 40° C. to 250° C. it is transferable in unexposed or insufficiently exposed areas.

Suitable thermoplastic polymers for use in connection with the present invention include the following:

(A) Polyesters and polyester mixtures of alkanediols, e.g. polymethylene glycol of the formula HO—(CH$_2$)$_v$—OH where v is an integer from 2 to 10, and two or more of the dicarboxylic acids: terephthalic acid, isophthalic acid, sebacic acid and hexahydrophthalic acid;

(B) nylons or polyamides, e.g. N-methoxymethyl polyhexamethyleneadipamide;

(C) vinylidene chloride copolymers, e.g. vinylidene/acrylonitrile, vinylidene chloride/methacrylate and vinylidene chloride/vinyl acetate copolymers;

(D) ethylene/vinyl acetate copolymers;

(E) cellulose ethers, e.g. methyl cellulose, ethyl cellulose and benzyl cellulose;

(F) polyethylene;

(G) synthetic rubbers, e.g. butadiene/acrylonitrile copolymers and polymers of 2-chloro-1,3-butadiene;

(H) cellulose esters, e.g. cellulose acetate, cellulose acetate succinate, cellulose acetate butyrate and cellulose nitrate;

(I) polyvinyl esters, e.g. polyvinyl acetate/acrylate, polyvinyl acetate/methacrylate and polyvinyl acetate;

(J) polyacrylates and polymethacrylates, e.g. polymethyl methacrylate;

(K) high molecular weight polyethylene oxides of polyglycols having an average molecular weight of about 4000 to 1,000,000;

(L) polyvinyl chloride and copolymers; e.g. polyvinyl chloride/acetate, polyvinyl chloride/acetate/alcohol;

(M) polyvinyl acetal, e.g. polyvinylbutyral or polyvinylformal;

(N) polyformaldehydes;

(O) polyurethanes;

(P) polycarbonates;

(Q) polystyrene and its copolymers, e.g polystyrene/acrylonitrile or polystyrene/acrylonitrile/butadiene.

Polymeric compounds which are not thermoplastic may also be added to the photopolymerisable composition in order to impart certain desired properties to the composition, e.g. to improve the adherence to the original support or to the support of the acceptor element after transfer and to improve the mechanical or chemical stability. Suitable non-thermoplastic polymeric compounds include polyvinyl alcohol cellulose, anhydrous gelatine, phenol resins and melamine formaldehyde resins. If desired, the photopolymerisable layers may also contain immiscible polymers or non-polymeric organic or inorganic fillers or reinforcing materials which are substantially transparent at the wavelengths used for exposure, e.g. organophilic silicon compounds, bentonites, silica, powdered glass, colloidal carbon and various types of dyes and pigments; these may be used in varying quantities, depending on the desired properties. The fillers may be used to improve the strength of the composition or reduce the tackiness and are also suitable as colouring agents.

Substances for improving the wetting or adherence of the thermoplastic layer may also be added. Suitable substances for this purpose are, for example, silicones, polymers containing silicon, e.g. a poly(dimethylsiloxane)polyether copolymer, poly(dimethylsiloxane)-polyesters, surface-active agents containing silicon, copolymers containing fluorine and wetting agents containing fluorine.

The monomers corresponding to the general Formula I may be mixed with other polymerisable ethylenically unsaturated compounds, for example the monomers disclosed in European Patent Application 91 200 468.6 (05.03.91). Other suitable polymerisable ethylenically unsaturated compounds which may be used according to the present invention include, for example, unsaturated esters of polyols, in particular those of α-methylene carboxylic acids, e.g. ethylene diacrylate, glycerol trimethacrylate, ethylene dimethacrylate, 1,3-propanediol dimethacrylate, 1,2,4-butanetriol trimethacrylate, 1,4-cyclohexanediol dimethacrylate, hydroquinone dimethacrylate, pentaerythritol tetramethacrylate, 1,5-pentanediol dimethacrylate, bisacrylates and methacrylates of polyethylene glycols having molecular weights from 200 to 500; unsaturated amides, in particular those of α,ω-diamines optionally interrupted by oxygen atoms, such as methylene-bisacrylamide, methylenebismethacrylamide, 1,6-hexamethylenebisacrylamide, diethylenetriamine-trismethacrylamide, bis-(γ-methacrylamidopropoxy)-ethane, β-methacrylamido-ethylmethacrylate, N-(β-hydroxyethyl)-β-(methacrylamido)-ethylacrylate and N,N-bis-(β-methacryloyloxyethyl)-acrylamide; vinyl esters, e.g. divinylsuccinate, divinyladipate, divinylphthalate and divinylbutane-1,4-disulphonate; and unsaturated aldehydes, e.g. hexadienal. Other suitable polymerisable ethylenically unsaturated compounds which may be used according to the present invention include polymers and/or oligomers having two or more polymerisable functions, e.g. acrylated epoxides, polyester acrylates and urethane acrylates.

The quantity of monomers according to the general Formula I and optionally of the comonomers varies with the individual thermoplastic polymers and/or other additives chosen.

The photopolymerisable composition according to the present invention also contains at least one photoinitiator. The photoinitiators used are preferably polymerisation initiators which are thermally inactive at temperatures below 185° C. and can be activated by actinic light. Examples of such initiators include substituted and unsubstituted multinuclear quinones, i.e. compounds having two carbonyl groups attached to ring carbon atoms in a conjugated 6-membered carbocyclic ring, with at least one aromatic carbocyclic ring condensed to the ring which carries the carbonyl groups. Such initiators include 9,10-anthraquinone, 1-chloroanthraquinone, 2-chloroanthraquinone, 2-methylanthraquinone, 2-tert.-butylanthraquinone, octamethylanthraquinone, 1,4-naphthoquinone, 9,10-phenanthrenequinone, 1,2-benz-anthraquinone, 2,3-dichloronaphtho-quinone, the sodium salt of anthraquinone-α-sulphonic acid, 3-chloro-2-methylanthraquinone and 1,2,3,4-tetrahydro-benzo[a]-anthracene-7,12-dione. Other suitable photoinitiators are described in U.S. Pat. No. 2,760,863 and include vicinal ketaldonyl compounds such as diacetyl, benzil, α-ketaldonyl alcohols such as benzoin, pivalone, acyloin ethers such as benzoin methyl and ethyl ethers; α-hydrocarbon-substituted aromatic acyloins including methylbenzoin, α-allylbenzoin and α-phenylbenzoin. Other suitable photoinitiators are described in "Photoreactive Polymers" by Arnost Reiser, "Organic photochemical imaging systems" by G.A. Delzenne in "UV-Curing Chemistry: Past, Present, and Future" by Christian Decker, published in Journal of Coatings Technology, Volume 59, No.751, August 1987, pages 97–106 and in EP-A-0 362 827 and U.S. Pat. No. 3,558,309.

According to the present invention, thermal polymerisation inhibitors may also be added to the photopolymerisable compositions. Examples of suitable inhibitors include p-methoxyphenol, hydroguinone, alkyl- and acyl-substituted hydroguinones and quinones, tert.-butylpyrocatechol, pyrogallol, copper compounds, naphthylamines, β-naphthol, copper-II-chloride, 2,6-bis-tert.-butyl-p-cresol, photothiazine, pyridine, nitrobenzene and dinitrobenzene, p-toluquinone and chloranil.

Various dyes, pigments, thermographic compounds, UV-absorbents, antioxidants and colour producing components may be added to the photopolymerisable compositions for obtaining numerous desired results after the transfer by heat. These additional substances should, however, absorb as little light as possible at the wavelength used for exposure and should as far as possible not inhibit the polymerisable reaction.

The following are dyes suitable for the invention: Fuchsine (C.I. 42510), Auramine Base (C.I. 410003), Calcocid Green S (C.I. 44000), Para Magenta (C.I. 42500), Tryparosan (C.I. 42505), New Magenta (C.I. 42520), Acid Violet RRL (C.I. 42425), Red Violet 5RS (C.I. 42960), C.I. Solvent Blue 36 (C. I. 61551), Nile Blue 2B (C. I. 51185), New Methylene Blue GG (C.I. 51195), C.I. Basic Blue 20 (C.I. 42585), Iodine Green (C.I. 42556), Night Green B (C.I. 42415), C.I. Direct Yellow 9 (C.I. 19540), C.I. Acid Yellow 17 (C.I. 18965), C.I. Acid Yellow 29 (C.I. 18900), Tartrazine (C.I. 191940), Supramine Yellow G (C.I. 19300), Buffalo Black 10B (C.I. 27790), Naphthalene Black 12R (C. I. 20350), Fast Black L (C. I. 51215) and Ethyl Violet (C.I.42600).

Suitable pigments include, for example, the following: $TiO_2$, colloidal carbon, graphite, phosphorus particles, ceramic particles, clay particles, metal powders such as aluminium, copper, magnetic iron and bronze. The pigments are particularly useful if they are incorporated in the photosensitive layer or in an adjacent light-insensitive layer, e.g. an antihalation layer or a layer for improving the adherence between the support and the photosensitive layer.

Suitable thermographic additives, e.g. 3-cyano-4,5-dimethyl-5-hydroxy-3-pyrrolin-2-one, and activators, e.g. copper acetate, are described in the following U.S. Pat. Nos.: 2,825,494, 2,637,657, 2,665,654, 2,663,655, 2,663,656 and 2,663,657.

The following are examples of suitable colour producing components which form coloured compounds when exposed to the action of heat or brought into contact with other colour producing components in an acceptor element:
(1) Organic and inorganic components: Dimethylglyoxime and nickel salts; phenolphthalein and sodium hydroxide; starch/potassium iodide and oxidizing agents, e.g. peroxides, phenols and iron salts; thioacetamide and lead acetate, silver salts and reducing agents, e.g. hydroquinone.
(2) Inorganic components: Iron-III salts and potassium thiocyanate; iron-II salts and potassium ferricyanide; copper and silver salts and sulphide ions; lead acetate and sodium sulphide.
(3) Organic components: 2,4-Dinitrophenylhydrazine and aldehydes or ketones; diazonium salts and phenol or naphthol, e.g. benzene diazonium chloride and β-naphthol; p-dimethylaminobenzaldehyde and p-diethylaminoaniline.

The image producing element according to the present invention may contain other layers, e.g. a layer for improving the adherence of the photopolymerisable layer to the layer support or a stripping layer. It is particularly advantageous to arrange a functional interlayer between the layer support and the light-sensitive photopolymerisable layer in a position directly adjacent to the latter. This interlayer may contain, for example, a polymer having polymerisable ethylenically unsaturated groups. Such a functional interlayer is described, for example, in European Patent Application 91 201 824.9 (12.07.91).

Layer supports suitable for the image producing element according to the invention are stable at the temperatures required for the transfer of the unexposed or insufficiently exposed parts of the photopolymerisable composition to the acceptor material. Examples of suitable supports include those of polyesters, e.g polyethylene terephthalate, glass, wood, paper, polyethylene coated paper, cellulose esters such as cellulose acetate, cellulose propionate or cellulose butyrate, polycarbonate, polyvinyl chloride, polyimide and polypropylene.

The acceptor material to which the image is transferred must also be stable at the operating temperatures. The acceptor material used in any particular case depends on the adherence of the image to the image producing element.

Suitable acceptor materials include paper, cardboard, and metal films and fabrics, e.g. of aluminium, copper, iron or bronze, polyethylene, polyesters, e.g. polyethylene terephthalate, polyesters which have been foamed up to render them opaque or pigmented polyesters, cellulose esters, silk, cotton, polycarbonate, polyvinyl chloride, polypropylene and polyethylene-backed paper.

The acceptor element may have a hydrophilic surface or contain a layer with preferential adherence to the unexposed parts of the layer of the photopolymerisable composition or its surface may contain compounds which react with the transferred compounds to produce a difference in colour, hydrophilic character, conductivity and the like on the surface of the acceptor material.

The image producing element and acceptor material may be brought into contact before exposure or provided as a unit element. Such an element is known as monosheet material and presupposes that either the front or the back is transparent to the radiation used for exposure of the photopolymerisable composition.

In a particularly preferred embodiment of the present invention, the acceptor material contains a hydrophilic surface. Transfer of the unexposed or insufficiently exposed parts of the photopolymerisable composition to an acceptor element having a hydrophilic surface results in an imagewise differentiation between hydrophilic and hydrophobic parts, which may be used for a printing process with oily or fatty ink. The hydrophobic parts are ready to accept lithographic ink while the hydrophilic parts do not accept ink, especially after they have been moistened with water. The parts coloured with ink constitute the printed image and the areas which repel ink form the image background.

After transfer of the unexposed or insufficiently exposed parts of the photopolymerisable composition, it may be advantageous to subject the transferred image to a uniform exposure or heating to improve the stability. Such a measure is particularly to be recommended when the transferred image is to be used as a printers copy.

Examples of acceptor materials having a hydrophilic surface include metal supports such as supports of aluminium or zinc, polyester films and paper supports. If these supports are not sufficiently hydrophilic, they may first be coated with a hydrophilic layer. One particularly suitable hydrophilic layer is a layer of polyvinyl alcohol which has been hardened with a tetraorthosilicate, e.g. a $TiO_2$-containing tetramethyl orthosilicate or tetraethyl orthosilicate, as described, for example, in U.S. Pat. No. 3 971 660.

Aluminium is a particularly suitable metal support. Aluminium foils of pure aluminium or an aluminium alloy having an aluminium content of at least 95% are suitable aluminium supports for use according to the present invention. A suitable alloy may contain, for example, 99.55% by weight of aluminium, 0.29% by weight of iron, 0.10% by weight of silicon, 0.004% by weight of copper, 0.002% by weight of manganese, 0.02% by weight of titanium and 0.03% by weight of zinc. The thickness of such a foil is normally from 0.13 to 0.5 mm.

The production of an aluminium foil or a foil of aluminium alloy suitable for lithographic offset printing comprises the following steps: Roughening, anodization and optionally sealing.

Roughening and anodization of the foil are necessary for obtaining high quality prints according to the present invention. Sealing is not necessary but may further improve the printing results.

Roughening of the aluminium surface may be carried out mechanically or electrolytically in known manner. The roughness obtained by roughening is measured in μm as the deviation from a mid-line and is preferably about 0.2 to 1.5 μm.

Anodization of the aluminium foil may be carried out in electrolytic baths, e.g. of chromic acid, oxalic acid, sodium carbonate, sodium hydroxide and mixtures thereof. The anodization of aluminium is preferably carried out in dilute aqueous sulphuric acid until the desired thickness of anodizing layer is obtained. The aluminium foil may be anodized on both sides. The thickness of the anodizing layer is accurately determined on a microsection but may equally well be determined by dissolving the anodizing layer and weighing the foil before and after this treatment. Good results are obtained with an anodizing layer about 0.4 to about 2.0 μm in thickness. To improve the image sharpness and hence the sharpness of the printed copy, the anodizing layer may be body-coloured with an antihalation dye or pigment, for example as described in JP-A-58-14797.

The anodic surface may be sealed after the anodizing treatment. Sealing of the pores of the aluminium oxide layer formed by anodizing is a known technique which has been described, for example, in "Belgisch-Nederlands tijdschrift voor Oppervlaktetechnieken van materialen", 24th Year/January 1980. Various types of sealing of porous anodized aluminium surfaces are known. One advantageous method is hydration sealing, in which the pores are partly or completely sealed by the absorption of water so that hydrated, needle-shaped aluminium oxide crystals (Böhmite) are formed. The anodized surface of the aluminium foil may be treated for this purpose with water at 70° to 100° C. or with steam. The water may contain additives, e.g. nickel salts, to improve the sealing effect. Sealing may also be carried out by treating the anodic surface with an aqueous solution of phosphate ions or silicates. The sealing treatment renders the anodic layer substantially non-porous so that it is suitable for the production of a relatively large number of prints. As a result of the sealing treatment, the occurrence of fogging in the non-image parts of the printing plate can to a large extent be avoided.

Roughening, anodization and sealing treatment of the aluminium foil may be carried out as described, for example, in U.S. Pat. No. 3 861 917.

The image-producing element of the present invention is equally suitable for the production of an electrostatic printers' copy. In this process, the photopolymerisable composition according to the present invention is transferred after imagewise exposure to an acceptor element containing a conductive surface or a surface having compounds which react with the transferred compounds so that an imagewise differentiation in electrical conductivity is obtained. The acceptor material used is preferably one which has a conductive surface, e.g. a polyethylene tere-phthalate support having a metallic layer, for example of aluminium. After transfer of the imagewise exposed photo-polymerisable composition to such a material, the parts where no transfer has taken place, which corresponds to the exposed parts of the photopolymerisable composition in the image producing element, remain conductive while the other parts have become non-conductive. An electrostatic printer's copy is thus obtained.

The acceptor material may be a support having a metal layer, for example of copper. A printed circuit may thus be produced by a subsequent etching treatment in which the photopolymerisable composition which had been transferred imagewise acts as photoresist.

Colour images may be produced according to another embodiment of the present invention. In this case, at least three image producing elements containing a yellow dye, a magenta dye and a cyan dye or corresponding dye pigments in or below the photopolymerisable composition are exposed imagewise with a blue, green or red colour separation of the original. A fourth image producing element containing a black dye or dye pigment may also be used. These image producing elements are successively heated in contact with the same acceptor element, e.g. a paper, to bring about the transfer of the individual, differing colour separations. The transfer of the various colour separations of the image must, of course, be carried out in correct registration to ensure faithful colour reproduction of the original image.

In another embodiment of the process according to the invention, images may be produced by means of a monosheet material having a transparent layer support containing, in the sequence stated, a light-sensitive layer containing the monomer according to the invention, a pigment layer and an acceptor layer which is either self-supporting or arranged on a second layer support. After imagewise exposure through the transparent layer support, the unhardened or insufficiently hardened parts of the light-sensitive layer penetrate the pigment layer during the subsequent development and are transferred to the acceptor layer together with the pigment. The acceptor layer may consist, for example, of paper or a polyester film.

The term "transferred" is to be understood to mean that the unhardened or insufficiently hardened parts of the light-sensitive layer continue to adhere to the acceptor layer together with the pigment when the acceptor layer is withdrawn from the image producing element after the thermal transfer. In this embodiment, the pigment layer should be sufficiently porous to enable the unhardened or insufficiently hardened parts of the light-sensitive layer to penetrate. For this reason, as little binder as possible is used in the pigment layer. Pigment layers which are free from binder are preferred. The pigments mentioned above are suitable pigments for this embodiment.

An image may also be produced by heating an imagewise exposed image producing element containing the photopolymerisable composition according to the present invention as outer layer to a temperature which is sufficient to render the unexposed or insufficiently exposed parts tacky while the exposed parts remain untacky due to photopolymerisation. During the subsequent treatment with a powder of a dye pigment, e.g. carbon black, the image may be developed since the pigment adheres to the tacky parts of the heated image producing element. After the image producing element carrying the colouring powder has cooled to room temperature, the image producing element may be exposed uniformly so that the powdered parts also harden. An image of high quality and high contrast is obtained.

The above described embodiments of the present invention are easy to handle and environmentally friendly owing to the dry development employed and are therefore preferred. It is clear to the man of the art, however, that the imagewise exposed photopolymerisable composition may equally well be developed in the presence of solvents for dissolving the unexposed or insufficiently exposed parts. Suitable solvents for use in such a development process are organic solvents, e.g. chloroform, dichloroethane, dichloromethane, toluene and benzene.

EXAMPLE 1 (PREPARATION OF THE MONOMERS)

General method of procedure

The isocyanate group content or OH group content of the isocyanates and hydroxyalkyl (meth) acrylates used were determined quantitatively by titration so that the reactive groups were used in exactly equimolar quantities.

The isocyanate (0.300 mol of NCO) was introduced into the reaction vessel in 250 ml of chloroform at room temperature and 600 ppm of Sn-II isooctanoate (Desmorapid SO) and 1000 ppm of 2,6-di-tert.-butylcresol (Jonol) were added. This reaction mixture was stirred and the hydroxyalkyl(meth)acrylate was added dropwise at room temperature over a period of 20 minutes to produce a slightly exothermic reaction which raised the temperature by about 5° C. Stirring was continued for 30 minutes and the reaction mixture was heated to 60° C. and left at this temperature until all the isocyanate groups had completely reacted in accordance with the IR check (complete reaction in most cases necessitated stirring overnight so that the reaction could not be stopped until the following morning).

Compound M-1 from Table 1

0.150 Mol of uretdione of hexamethylene diisocyanate was reacted with 0.300 mol of 2-hydroxyethylacrylate in accordance with the general method of procedure.

Compound M-2 from Table 1

0.150 Mol of uretdione of hexamethylene diisocyanate was reacted with 0.300 mol of 2-hydroxyethylmethacrylate in accordance with the general method of procedure,

Compound M-3 from Table 1

0.150 Mol of uretdione of hexamethylene diisocyanate was reacted with 0,300 mol of glycerol dimethacryiate in accordance with the general method of procedure.

Compound M-4 from Table 1

0.150 Mol of uretdione of hexamethylene diisocyanate was reacted with 0.300 mol of pentaerythritol triacrylate in accordance with the general method of procedure.

Compound M-5 from Table 1

0.150 Mol of uretdione of 1,3-diisocyanato-4-methylcyclohexane was reacted with 0,300 mol of glycerol dimethacrylate in accordance with the general method of procedure.

Compound M-6 from Table 1

0.100 Mol of biuret of hexamethylene diisocyanate (Desmodur N 100 of Bayer AG) was reacted with 0.300 mol of glycerol dimethacrylate in accordance with the general method of procedure.

Compound M-7 from Table 1

0.100 Mol of isocyanurate of hexamethylene diisocyanate (Desmodur N 3300 of Bayer AG) was reacted with 0.300 mol of glycerol dimethacrylate in accordance with the general method of procedure.

EXAMPLE 2

An image producing element was prepared as follows:

The following were applied (per $m^2$) to a layer support of polyethylene terephthalate 100 $\mu$m in thickness covered with an adhesive layer:
  a) a functional interlayer (1 g) of polyvinyl alcohol containing 25 mol-% of hydroxyl groups modified by a reaction with methacrylic dichloride;
  b) a photosensitive layer (3 g) cast as a solution in methyl ethyl ketone of:

| | |
|---|---|
| 4% by weight | monomer M-3 |
| 0.66% by weight | blue dye (C.I. 61551) |
| 0.02% by weight | TEGOGLIDE 410 (polysiloxane-polyether copolymer of Goldschmidt AG, Essen) |
| 3.5% by weight | bisimidazole |
| 0.1% by weight | Michlers ketone |
| 0.2% by weight | mercaptobenzoxazole. |

An acceptor element was prepared as follows:

The following were added successively with stirring to 418 g of a dispersion of 21.5% by weight of $TiO_2$ (average particle size 0.3 to 0.5 $\mu$m) and 2.5% by weight of polyvinyl alcohol in deionised water:
  220 g of a 5% solution of polyvinyl alcohol in water
  95 g of a hydrolysed 22% emulsion of tetramethylorthosilicate in water
  22 g of a 10% solution of a wetting agent.
  245 ml of deionised water were then added to this mixture and the pH was adjusted to 4. This dispersion was cast on a layer support covered with a hydrophilic adhesive layer to form thereon a layer having a wet thickness of 55 g which was then dried at 30° C.

The image producing element was brought into contact with a transparent test original having a line pattern of 150 lines per inch and exposed to UV light through this test original.

The exposed image producing element was then passed through laminator rollers at 165° C. and at a speed of 1.02 m/min while in contact by its coated surface with the hydrophilic acceptor element.

The sample showed good point reproduction. The image obtained on the acceptor element could be used for printing in a conventional offset printing device with conventional ink followed by rinsing. Good copies were obtained.

EXAMPLE 3

An image producing element was prepared as in Example 2 but using monomer M-6 instead of monomer M-3. Exposure and processing were carried out as in Example 2. Good point reproduction was obtained.

The sample showed good point reproduction. The image obtained on the acceptor element could be used for printing in a conventional offset printing device with conventional ink followed by rinsing. Good copies were obtained.

EXAMPLE 4

An image producing element was prepared as in Example 2 but using monomer M-7 instead of monomer M-3. Exposure and processing were carried out as in Example 2. Good point reproduction was obtained.

The sample showed good point reproduction. The image obtained on the acceptor element could be used for printing in a conventional offset printing device with conventional ink followed by rinsing. Good copies were obtained.

EXAMPLE 5

An image producing element was prepared as described in Example 2 but in this case the functional interlayer had an application of 2 g and the photopolymerisable layer an application of 1 g and the photopolymerisable layer was covered with a pigment layer containing 5% by weight of carbon black and having a dry layer thickness of 1 g.

The image producing element obtained was exposed imagewise as described in Example 2 and then passed through a set of laminating rollers at 180° C. and a velocity of 0.36 m/min while in contact with a polyethylene terephthalate support as image acceptor material. The elements were then pulled apart. An image with high resolution was obtained.

EXAMPLE 6

An image producing element was prepared as described in Example 5 but monomer M-6 was used instead of monomer M-3. Exposure and processing were carried out as indicated in Example 5. Good point reproduction was obtained.

EXAMPLE 7

An image producing element was prepared as described in Example 5 but using monomer M-7 instead of monomer M-3. Exposure and processing were carried out as described in Example 5. Good point reproduction was obtained.

We claim:

1. Image producing element having a layer of photopolymerisable composition applied to a layer support, characterised by a photopolymerisable content of at least one monomer corresponding to the following formula

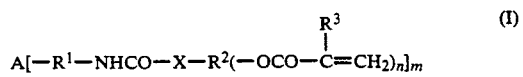

wherein
A denotes a double-bonded or triple-bonded condensed urea group selected from the group consisting of

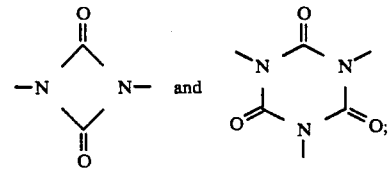

X denotes —O— or —NR— in which $R=C_1-C_{12}$-alkyl;
$R^1$ denotes a double-bonded hydrocarbon group having 2 to 25 carbon atoms;
$R^2$ denotes a triple-bonded to six-bonded linear or branched
hydrocarbon group with 2 to 18 carbon atoms optionally
interrupted by up to 3 O-atoms;
$R^3$ denotes H or methyl;
n denotes an integer from 2 to 5; and
m stands for 2 or 3.

2. Image producing element according to claim 1, characterised in that the photopolymerisable composition contains from 3 to 97% by weight of one or more monomers of Formula I and 97 to 3% by weight of thermoplastic polymer.

3. Image producing element according to claim 2, characterised in that the photopolymerisable composition contains a dye or a colour pigment.

4. Image producing element according to claim 2, characterised in that a functional interlayer containing a polymer having polymerisable ethylenically unsaturated groups is arranged between the layer support and the photopolmerisable layer in a position adjacent to the latter.

5. Image producing element according to claim 2, characterised in that an acceptor layer is arranged above the photopolymerisable layer (monosheet material).

6. Image producing process in which an image producing element according to claim 2 is exposed imagewise to actinic radiation whereby the imagewise exposed parts of the photopolymerisable layer are hardened, and in which the parts of the photopolymerisable layer which are not hardened or insufficiently hardened are transferred to an acceptor layer by heating.

7. Image producing element according to claim 1, characterised in that the photopolymerisable composition contains a dye or a colour pigment.

8. Image producing element according to claim 7, characterised in that a functional interlayer containing a polymer having polymerisable ethylenically unsaturated groups is arranged between the layer support and the photopolymerisable layer in a position adjacent to the latter.

9. Image producing element according to claim 7, characterised in that an acceptor layer is arranged above the photopolymerisable layer (monosheet material).

10. Image producing process in which an image producing element according to claim 7 is exposed imagewise to actinic radiation whereby the imagewise exposed parts of the photopolymerisable layer are hardened, and in which the parts of the photopolymerisable layer which are not hardened or insufficiently hardened are transferred to an acceptor layer by heating.

11. Image producing element according to claim 1, characterised in that a functional interlayer containing a polymer having polymerisable ethylenically unsaturated groups is arranged between the layer support and the photopolymerisable layer in a position adjacent to the latter.

12. Image producing element according to claim 11, characterised in that an acceptor layer is arranged above the photopolymerisable layer (monosheet material).

13. Image producing process in which an image producing element according to claim 11 is exposed imagewise to actinic radiation whereby the imagewise exposed parts of the photopolymerisable layer are hardened, and in which the parts of the photopolymerisable layer which are not hardened or insufficiently hardened are transferred to an acceptor layer by heating.

14. Image producing element according to claim 1, characterised in that an acceptor layer is arranged above the photopolymerisable layer (monosheet material).

15. Image producing process in which an image producing element according to claim 14 is exposed imagewise to actinic radiation whereby the imagewise exposed parts of the photopolymerisable layer are hardened, and in which the parts of the photopolymerisable layer which are not hardened or insufficiently hardened are transferred to an acceptor layer by heating.

16. Image producing element according to claim 6, characterised in that a pigment layer is arranged between the photopolymerisable layer and the acceptor layer.

17. Image producing process in which an image producing element according to claim 16 is exposed imagewise to actinic radiation whereby the imagewise exposed parts of the photopolymerisable layer are hardened, and in which the parts of the photopolymerisable layer which are not hardened or insufficiently hardened are transferred to an acceptor layer by heating.

18. Image producing process in which an image producing element according to claim 1 is exposed imagewise to actinic radiation whereby the imagewise exposed parts of the photopolymerisable layer are hardened, and in which the parts of the photopolymerisable layer which are not hardened or insufficiently hardened are transferred to an acceptor layer by heating.

* * * * *